(12) United States Patent
Kern et al.

(10) Patent No.: US 9,921,214 B2
(45) Date of Patent: Mar. 20, 2018

(54) METHOD FOR PERFORMING A BIOCHEMICAL ANALYSIS, ESPECIALLY IN OUTER SPACE

(71) Applicant: Astrium GmbH, Taufkirchen (DE)

(72) Inventors: Peter Kern, Salem (DE); Herbert Backes, Saarbrucken (DE); Ulrich Kubler, Markdorf (DE)

(73) Assignee: Airbus DS GmbH, Taufkirchen (DE)

( * ) Notice: Subject to any disclaimer, the term of this patent is extended or adjusted under 35 U.S.C. 154(b) by 0 days.

(21) Appl. No.: 13/969,044

(22) Filed: Aug. 16, 2013

(65) Prior Publication Data
US 2014/0057290 A1 Feb. 27, 2014

(30) Foreign Application Priority Data
Aug. 21, 2012 (DE) .................. 10 2012 107 651

(51) Int. Cl.
| | | |
|---|---|---|
| G01N 33/53 | (2006.01) | |
| G01N 33/537 | (2006.01) | |
| G01N 33/543 | (2006.01) | |
| G01N 35/00 | (2006.01) | |

(52) U.S. Cl.
CPC ....... *G01N 33/5306* (2013.01); *G01N 33/537* (2013.01); *G01N 33/54326* (2013.01); *G01N 2035/00336* (2013.01)

(58) Field of Classification Search
None
See application file for complete search history.

(56) References Cited

U.S. PATENT DOCUMENTS

| | | | |
|---|---|---|---|
| 5,173,262 A | 12/1992 | Burtis et al. | |
| 6,030,792 A * | 2/2000 | Otterness | C07K 16/18 435/7.1 |
| 6,100,079 A | 8/2000 | Tajima | |
| 6,150,182 A * | 11/2000 | Cassaday | 436/526 |
| 7,271,009 B1 * | 9/2007 | Watkins et al. | 436/526 |
| 2003/0095897 A1 | 5/2003 | Grate et al. | |
| 2003/0134316 A1 | 7/2003 | Tashiro et al. | |
| 2004/0096857 A1 | 5/2004 | Machida et al. | |
| 2005/0250141 A1 * | 11/2005 | Lambert et al. | 435/6 |
| 2006/0286563 A1 | 12/2006 | Lin et al. | |
| 2007/0215553 A1 * | 9/2007 | Yellen et al. | 210/695 |
| 2008/0280377 A1 * | 11/2008 | Moore et al. | 436/501 |
| 2009/0168052 A1 * | 7/2009 | Burrell et al. | 356/73 |
| 2009/0311724 A1 | 12/2009 | Levison et al. | |
| 2010/0157724 A1 * | 6/2010 | Rida | 366/273 |
| 2010/0184022 A1 | 7/2010 | Colau | |
| 2010/0248258 A1 | 9/2010 | Lee et al. | |
| 2011/0025315 A1 | 2/2011 | Ohtsuka | |
| 2012/0178186 A1 | 7/2012 | Nieuwennhuis et al. | |

FOREIGN PATENT DOCUMENTS

| | | |
|---|---|---|
| CN | 1650162 A | 8/2005 |
| CN | 101545902 A | 9/2009 |
| CN | 101988922 A | 3/2011 |
| CN | 102597774 A | 7/2012 |
| DE | 695 18 321 T2 | 1/2001 |
| EP | 2 634 579 A1 | 9/2013 |
| JP | 04-507288 A | 12/1992 |
| JP | H04-507288 | 12/1992 |
| JP | 2002-181821 A | 6/2002 |
| JP | 2003-248008 A | 9/2003 |
| JP | 2005-312353 A | 11/2005 |
| JP | 2007-271411 A | 10/2007 |
| JP | 2009-523416 | 6/2009 |
| JP | 2009-523416 A | 6/2009 |
| JP | 2009-236933 | 10/2009 |
| JP | 2009-250814 A | 10/2009 |
| WO | 9933559 A1 | 7/1999 |
| WO | 2005/093641 A1 | 10/2005 |

OTHER PUBLICATIONS

Youngeun Kwon et. al.: "Magnetic Bead Based Immunoassay for Autonomous Detection of Toxins", Analytical Chemistry; vol. 80, No. 22, pp. 8416-8423.
Y. Moser et. al.: "Active Superparamagnetic Bead Manipulation for Immunoassays On-chip", The Proceedings of [Micro] TAS 2008 Conference, pp. 1372-1374.
Extended European Search Report dated Nov. 5, 2013 in the corresponding EP application No. 13175746.0/1405 (Partial English translation).
Office Action dated Jul. 8, 2014 in corresponding JP Application No. 2013-168401 (with English translation).
Office Action dated Mar. 17, 2015 issued in corresponding CN patent application No. 201310366311.5 (and English translation).
Office Action dated Apr. 30, 2015 issued in corresponding CA patent application No. 2,823,927.
Office Action dated Jun. 9, 2015 issued in corresponding JP patent application No. 2013-168401 (and English translation).
Office Action dated Mar. 4, 2016 issued in corresponding EP patent application No. 13175746.0 (and partial English translation).
Office Action dated Mar. 11, 2016 issued in corresponding CA patent application No. 2,823,927.
ffice Action issued Nov. 4, 2015 in the corresponding Cn application No. 201310366311.5 (with English ranslation) X.
Office Action dated Oct. 4, 2016 issued in corresponding JP patent application No. 2015-176840 (English ranslation attached).
Office Action dated Jun. 12, 2016 issued in corresponding CN patent application No. 201310366311.5 (and English summary provided by Chinese colleagues).

(Continued)

*Primary Examiner* — Christine Foster
*Assistant Examiner* — Ellen J Marcsisin
(74) *Attorney, Agent, or Firm* — Posz Law Group, PLC

(57) ABSTRACT

The invention is based on a method for performing a biochemical analysis, especially in outer space, wherein at least one analyte in a sample is determined qualitatively and/or quantitatively by means of selective binding of an analyte-specific pair composed of a binding substance and a detection substance to the analyte and by labeling by a labeling substance, and wherein the sample, the binding substance, the detection substance and the labeling substance are mixed in a reaction vessel in one method step. It is proposed that the mixing be brought about by means of mixing bodies.

2 Claims, 2 Drawing Sheets

(56) References Cited

OTHER PUBLICATIONS

Figure 1:
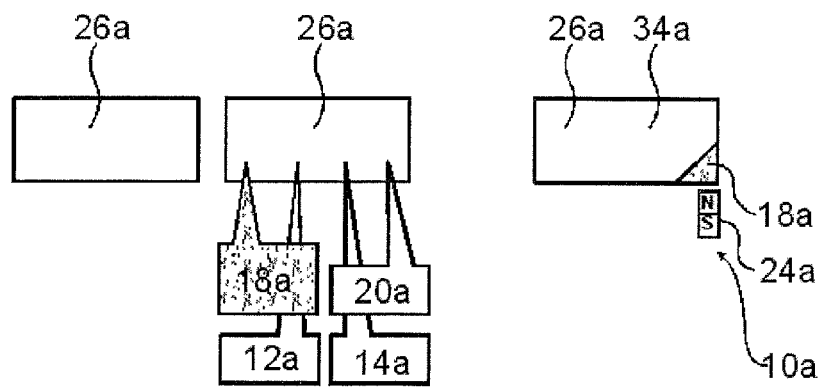

Office Action dated Mar. 8, 2017 issued in corresponding CN patent application No. 201310366311.5 (and English summary of the Office Action).
Search Report issued in corresponding DE patent application No. 10 2012 107 651.0 (and partial English translation).

* cited by examiner

METHOD FOR PERFORMING A BIOCHEMICAL ANALYSIS, ESPECIALLY IN OUTER SPACE

CROSS REFERENCE TO RELATED APPLICATIONS

This application is based on and incorporates herein by reference German Patent Application No. 10 2012 107 651.0 filed on Aug. 21, 2012.

PRIOR ART

The invention relates to a method for performing a biochemical analysis, especially in outer space.

A frequently used biochemical analytical technique for qualitatively and/or quantitatively detecting an analyte in a sample is provided by the methods referred to as immunoassays. Immunoassays are based on the functional principle of selective binding of an analyte in the sample by an analyte-specific pair of capture antibodies (cAB) and detection antibodies (dAB), with the latter bearing bound to themselves a labeling substance or being intended for binding of the labeling substance over the course of the method. The capture antibodies are intended to fix the analyte in a defined position, for example at a surface to which the capture antibodies are bound, or to carrier particles for the capture antibodies. The detection antibody selectively binds to the analyte or to the capture antibody. By means of the labeling substance, a measurable signal is produced which is intended to allow detection of a resulting analyte complex composed of analyte, capture antibody and detection antibody. In the immunoassays referred to as so-called enzyme-linked immunosorbent assays (ELISAs), the analyte is labeled as a labeling substance by means of an enzyme, which is present fixed to the detection antibody or is bound to the detection antibody in a further reaction step, wherein a chromogenic or a luminescent compound, for example a chemiluminescent, electroluminescent, bioluminescent or fluorescent compound, is generated from an added substrate in a subsequent enzyme-catalyzed reaction, which compound can be detected using optical techniques. To avoid signal saturation of the chromogenic or luminescent compound, a stopper is added after a predefined period to interrupt the enzyme-catalyzed reaction. The stopper can cause the interruption by, for example, a change in pH, wherein by means of the pH change, a resulting product from the reaction of the substrate with the enzyme is frequently made visible in the manner of a pH indicator. In the case of so-called radioimmunoassays (RIAs), radioactive substances are used as labeling substances bound to the detection antibody, with the analyte being quantitatively determined via measurement of radioactivity. Especially for precise quantitative determination of the analyte, it is necessary to carefully mix the sample, the capture antibodies, the detection antibodies and the labeling substance. In the case of applying an immunoassay on Earth, diffusive mass transfer as a result of the action of the Earth's gravity can suffice to attain sufficient mixing or a reaction vessel is mechanically moved, for example shaken.

Advantages of the Invention

The invention is based on a method for performing a biochemical analysis, especially in outer space, wherein at least one analyte in a sample qualitatively and/or quantitatively by means of selective binding of an analyte-specific pair composed of a binding substance, which fixes the analyte, and a detection substance, which bears bound to itself or binds to itself a labeling substance for quantification of the analyte, and wherein the sample, the binding substance, the detection substance and the labeling substance are mixed in a reaction vessel in one method step. In principle, when mixing the sample, the binding substance, the detection substance and the labeling substance in the reaction vessel, it is possible for solvents and other auxiliaries to be also present in the reaction vessel. Such a biochemical analysis is referred to as an immunoassay. "Performance in outer space" is to be understood to mean in particular that the biochemical analysis is performed beyond Earth, for example in a spacecraft in Earth orbit or at a Lagrange point, during a spaceflight or an orbit around another planet or a moon, on a satellite, a moon, an asteroid or on a planet other than Earth. More particularly, the performance in outer space can take place under conditions of reduced gravity. "Conditions of reduced gravity" are to be understood to mean in particular conditions in which a gravity effect of maximally 0.9 g, advantageously maximally $1*10^{-3}$ g, preferably maximally $1*10^{-6}$ g and particularly preferably maximally $1*10^{-8}$ g is effective. The value of 9.81 $m/s^2$ for acceleration due to gravity on Earth is designated "g".

"Biochemical analysis" is to be understood to mean in particular qualitative and/or quantitative analysis of a biochemical substance mixture for an analyte. An "analyte" is to be understood to mean in particular a chemical element or a chemical substance, for example a class of molecule or a specific molecule or macromolecule such as a protein, which, in a substance mixture, is to be tested qualitatively, i.e., merely for its presence, and/or quantitatively, i.e., for its concentration and/or quantity. A "sample" is to be understood to mean in particular a substance mixture to be analyzed, preferably a complex biological matrix, for example blood, blood plasma or serum, urine, saliva or other solutions. A "binding substance" is to be understood to mean in particular a substance which is intended to bind the analyte to itself. More particularly, the binding substance can be formed by a protein, preferably an antibody. A "detection substance" is to be understood to mean in particular a substance which can bind to the analyte or the binding substance and which bears bound to itself the labeling substance or is intended to bind the labeling substance to itself. More particularly, the detection substance can be formed by a protein, preferably an antibody. A "labeling substance" is to be understood to mean in particular a substance which is bound to the detection substance or can bind thereto and which is intended to generate a signal for quantification of the analyte and for detection of an analyte complex composed of the analyte, the binding substance and the detection substance. The labeling substance can, for example, be implemented as a dye or a fluorophore or an enzyme which catalyzes a signal-producing reaction, for example a color change due to substrate breaking-up. An "analyte-specific pair composed of a binding substance and a detection substance" is to be understood to mean in particular that the binding substance is intended to specifically bind to the analyte and the detection substance is specifically intended to bind to the analyte or to the binding substance and that the binding substance and the detection substance preferably have a low capacity for binding to further substances, especially to possible further analytes, in the substance mixture. A "reaction vessel" is to be understood to mean in particular a vessel specifically intended for performance of an analysis, having a work volume within which the reaction takes place.

It is proposed that the mixing be brought about by means of mixing bodies. "Mixing bodies" are to be understood to mean in particular bodies which are specifically intended to bring about mixing of at least two different substances and/or substance mixtures to form a joint substance mixture. More particularly, the mixing bodies are set in motion by an internal movement device or by an external force and, owing to their movement, mix the various substances and/or substance mixtures. A method having advantageous, rapidly and reliably performable mixing and a rapid process sequence can be achieved in particular. Furthermore, it is possible in particular to achieve rapid mixing even under conditions of reduced gravity, for example in outer space, in which diffusive mass transfer proceeds only very slowly.

It is further proposed that the mixing be brought about by means of magnetically moved mixing bodies. "Magnetically moved mixing bodies" are to be understood to mean in particular mixing bodies which can be set in motion, more particularly translational or rotational motion, by an applied magnetic field, preferably an alternating magnetic field. Mixing realizable with low complexity in terms of apparatus can be achieved in particular.

It is further proposed that the mixing be brought about by means of magnetic inert bodies. "Magnetic inert bodies" are to be understood to mean in particular magnetic or magnetizable particles which are specifically designed to be free of binding capabilities with respect to substances in the sample, binding substances, detection substances and labeling substances. More particularly, the magnetic inert bodies are free of analyte-specific detection substances or analyte-specific binding substances bound to the bodies. High process efficiency and unimpeded progression of the biochemical analysis can be achieved in particular.

It is further proposed that the mixing be brought about by means of magnetic carrier bodies for the analyte-specific binding substance or for the analyte-specific detection substance. "Magnetic carrier bodies" are to be understood to mean in particular magnetic or magnetizable particles which bear bound to themselves the analyte-specific binding substance and/or the detection substance, for example on the basis of a covalent or an adsorptive bond. More particularly, the magnetic carrier bodies are intended to be positioned by means of a magnetic field for a readout after a chemical reaction in the analysis has been completed. Advantageous functional integration can be achieved in particular.

It is further proposed that the binding substance and/or the detection substance be used in at least one method step in an at least substantially anhydrous form. An "at least substantially anhydrous form" is to be understood to mean in particular a form in which the binding substance and/or the detection substance are present as a solid, it being possible for the interior of the solid to contain water and/or an appropriate additive at a proportion which is sufficient to prevent functional damage to the binding substance and/or the detection substance. More particularly, the binding substance and/or the detection substance can be brought into solution in a further method step. Simple and space-saving storage of the binding substance and/or the detection substance can be achieved in particular.

It is further proposed that the binding substance and/or the detection substance be brought into solution in at least one further method step. More particularly, the binding substance and the detection substance can be stored in separate chambers and be contacted with one another by means of continued flowing of solvents and introduced into the reaction vessel. Alternatively, the binding substance and the detection substance can be stored in the same chamber and be brought into solution simultaneously. Advantageous mixing can be achieved in particular.

It is further proposed that a binding substance fixed undetachably at a spatially predefined site of the reaction vessel be used. "Fixed undetachably" is to be understood to mean in particular that the binding substance remains fixed at the spatially predefined site upon addition of further substances during the biochemical analysis, more particularly the sample and the detection substance and also solvents, and upon mixing of the further substances. More particularly, the binding substance is arranged at a position advantageous for a readout of a signal generated by the labeling substance for quantification of the analyte. An easily performable readout can be achieved in particular.

It is further proposed that the mixing be carried out under conditions of reduced gravity. Disruptive conditions, such as gravity-induced sedimentation of stored substances or phase separation of substances within a substance mixture, can be reduced in particular.

It is further proposed that the carrier bodies be positioned by means of a magnet unit for a readout. A "readout" is to be understood to mean in particular detection and quantitative evaluation of at least one signal generated by the labeling substance for quantitative detection of the analyte. In addition, the readout can, for example, be achieved by a spatial resolution or as an integral measured value over an entire detection space and/or be coupled to an image processing system. "Positioned for a readout" is to be understood to mean in particular that the carrier bodies are positioned within a reaction vessel by means of the magnet unit for a readout, preferably a readout by means of optical techniques, in such a way that a readout with high precision is possible. More particularly, the carrier bodies are positioned for this purpose in a planar manner within the detection space, so that they preferably form a thin layer. A readout easily realizable in terms of apparatus can be achieved in particular.

It is further proposed that positioning of the mixing bodies for a readout be brought about by means of artificially generated gravity. More particularly, the mixing is brought about by means of centrifugation or by means of shaking and subsequent sedimentation of the mixing bodies. Positioning easily realizable in terms of apparatus can be achieved in particular.

Further proposed is at least a second analyte-specific pair of binding substances and detection substances which is intended for determination of a further analyte. In principle, it is possible to use any desired large number of analyte-specific pairs of binding substances and detection substances which are intended for determination of further analytes. The detection substances can bear bound to themselves the same labeling substance or different labeling substances. It is possible in particular to determine multiple analytes in a single reaction and thus save time and additional equipment.

It is further proposed that magnetic carrier bodies for different analyte-specific binding substances or for different analyte-specific detection substances be distinguishable from one another in a readout. "Be distinguishable from one another in a readout" is to be understood to mean in particular that the carrier bodies for different analyte-specific binding substances or for different analyte-specific detection substances send out measurement signals which differ from one another and differ from a signal of the labeling substance, such that they can be distinguished in a readout from one another and from a signal of the labeling substance. For example, the carrier bodies can be designed in such a way that a carrier body for a binding substance for a first analyte sends out, after irradiation with light, a fluorescent signal, the wavelength of which differs from the wavelength of a fluorescent signal of a carrier body for a binding substance for a second analyte and of a fluorescent signal of a labeling substance, such that a quantitative determination of the first and the second analyte is possible from measured fluorescent signals of the carrier bodies of the binding substances and of the labeling substance in a readout. Alternatively, the carrier bodies can also be distinguishable from one another in a readout on the basis of different geometric properties, for example differing diameter. It is possible in particular to undertake a quantitative determination of multiple analytes using a single readout step and to save time and reduce complexity in terms of apparatus.

Further proposed is a device containing mixing bodies which are intended for mixing the sample, the binding substance and the detection substance. Reliable mixing, especially under microgravity conditions, can thus be achieved in particular.

It is further proposed that the mixing bodies be implemented as magnetically movable mixing bodies. Reliable mixing with low complexity in terms of apparatus and construction can thus be achieved in particular.

It is further proposed that the mixing bodies be implemented as magnetic inert bodies. A device for performing a biochemical analysis that is universally usable and nonspecific can thus be achieved.

It is further proposed that the mixing bodies be implemented as magnetic carrier bodies for the analyte-specific binding substance or for the analyte-specific detection substance. An advantageous functional integration can be achieved in particular.

DRAWINGS

Further advantages are revealed by the following description of the drawings. The drawings show five exemplary embodiments of the invention. The drawings, the description and the claims contain numerous features in combination. A person skilled in the art will appropriately also consider the features individually and combine them to form further meaningful combinations.

Figure 2:
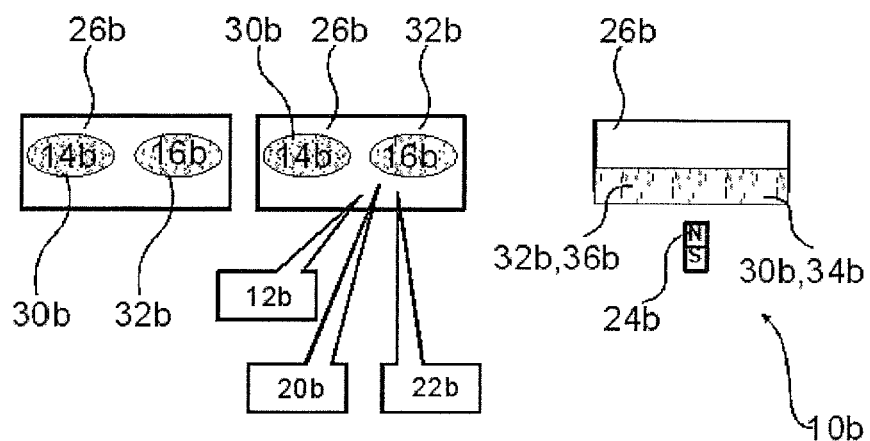
Figure 3:
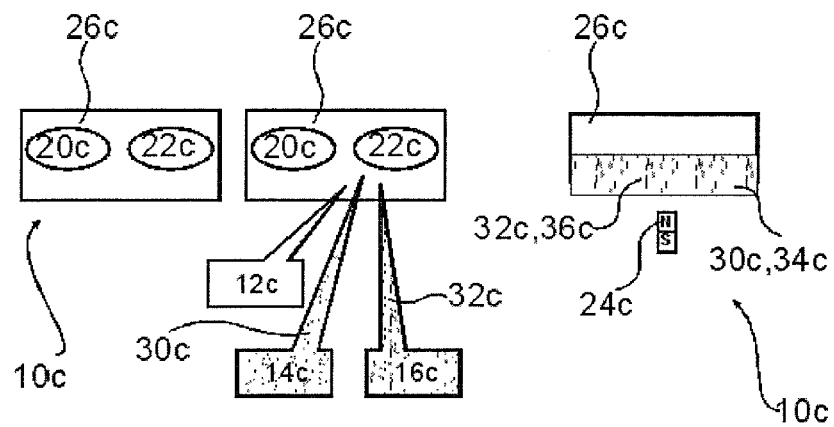
Figure 4:
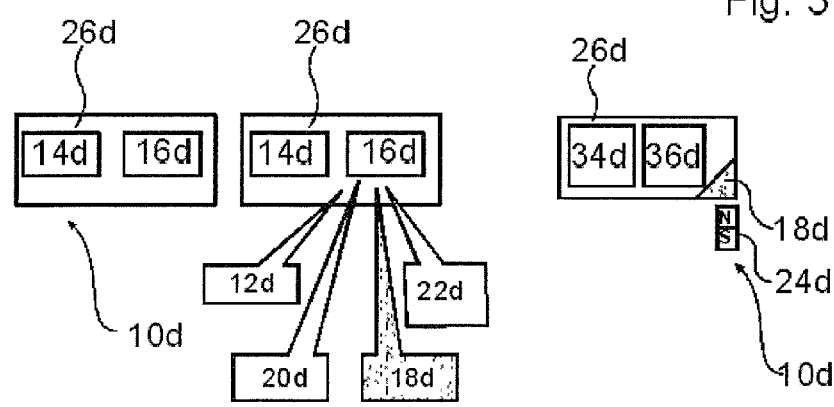
Figure 5:
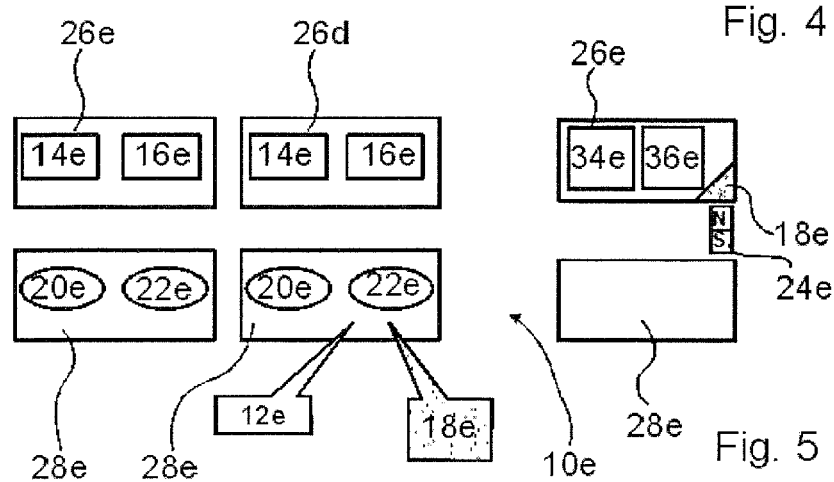

Shown by:

FIG. 1 is a first exemplary embodiment of a method for performing a biochemical analysis, in which mixing is brought about by means of magnetic inert bodies, FIG. 2 is a further exemplary embodiment of a method for performing a biochemical analysis, in which two analytes in a sample are determined and mixing is brought about by means of magnetic carrier bodies for detection substances, FIG. 3 is a further exemplary embodiment analogous to FIG. 2, in which mixing is brought about by means of magnetic carrier bodies for binding substances, FIG. 4 is a further exemplary embodiment of a method for performing a biochemical analysis, in which two stationary binding substances in a reaction vessel are used and mixing is brought about by means of magnetic inert bodies, and FIG. 5 is a further exemplary embodiment analogous to FIG. 3, in which an additional loading vessel is used.

DESCRIPTION OF THE EXEMPLARY EMBODIMENTS

FIG. 1 shows a first embodiment of a method for performing a biochemical analysis in outer space, wherein an analyte in a sample 12a qualitatively and quantitatively by means of selective binding of an analyte-specific pair composed of a binding substance 14a, which fixes the analyte, and a detection substance 20a, which bears bound to itself a labeling substance for labeling the analyte, and wherein the sample 12a, the binding substance 14a, the detection substance 20a and the labeling substance are mixed in a reaction vessel 26a in one method step. The method is designed as an immunoassay, such that the binding substance 14a is implemented as a capture antibody and the detection substance 20a is implemented as a detection antibody. The immunoassay is further designed as an enzyme-linked immunosorbent assay (ELISA), such that the labeling substance is implemented as an enzyme for breaking up a substrate which is added over the course of the method and which, after break-up, generates a visible color change. In alternative embodiments of the method, the labeling substance can, for example, be implemented as an enzyme which breaks up a substrate for generation of a fluorescent signal or as a fluorophore or another suitable signal-producing substance, and, in addition, the labeling substance can be introduced separately into the reaction vessel 26a and only bind to the detection substance 20a over the course of the method instead of being bound to the detection substance 20a at the start of the method. The method is performed in a device 10a comprising the reaction vessel 26a and a magnet unit 24a. The reaction vessel 26a is made from a transparent cyclic olefin copolymer having an advantageously low nonspecific binding capacity. Alternatively, the reaction vessel 26a can also be made from a different plastic, for example polystyrene. The plastic is preferably transparent, allowing a readout of labeled analytes by means of optical techniques. Alternatively, by appropriately selecting the labeling substance bound to the analyte-specific detection substance 20a, a readout by means of radiometric techniques is possible. The device 10a further comprises magnetically moved mixing bodies which are implemented as magnetic inert bodies 18a. The magnetic inert bodies 18a consist of a magnetically polarizable material which has a low nonspecific binding capacity and has in particular a low binding capacity with respect to the analyte in the sample 12a, the binding substance 14a, the detection substance 20a and the labeling substance.

In a first method step, the reaction vessel 26a is completely empty. In a further method step, the magnetic inert bodies 18a, the sample 12a and also the binding substance 14a, the detection substance 20a and the labeling substance together with further auxiliaries in a solution are introduced simultaneously into the reaction vessel 26a. In alternative embodiments, the magnetic inert bodies 18a, the sample 12a and also the binding substance 14a, the detection substance 20a and the auxiliaries can be introduced successively in multiple substeps into the reaction vessel 26a. The mixing is brought about by means of magnetically moved mixing bodies. The mixing bodies are implemented as the magnetic inert bodies 18a. The magnet unit 24a is implemented as an electromagnet which sets the magnetic inert bodies 18a in motion by means of an alternating magnetic field, bringing about the mixing of the sample 12a, the binding substance 14a and the detection substance 20a. Alternatively, the magnet unit 24a can also be implemented as a movably mounted permanent magnet which is itself set in motion to achieve a locally and temporally varying magnetic field within the reaction vessel 26a. Performance of the method, and the mixing in particular, is carried out under conditions of reduced gravity in outer space. However, the method can also be performed, for example, on an asteroid, a moon or an alien planet, on board a spacecraft located in Earth orbit or at a Lagrange point, and in principle even on Earth. During and after the mixing, the binding substance 14a and the detection substance 20a with the labeling substance bound thereto bind to the analyte from the sample 12a and form therewith an analyte complex 34a. After the mixing, in the method shown in the form of an ELISA, the substrate for signal generation is introduced into the reaction vessel 26a and broken up by the labeling substance for a color change. After a defined period, dependent on the analyte to be detected and on the labeling substance, after the mixing of the sample 12a, the binding substance 14a and the detection substance 20a, a stopper is introduced into the reaction vessel 26a, which stopper stops the conversion of the substrate by the labeling substance and/or stops a color change of a reaction product of the broken-up substrate in order to avoid signal saturation. For a readout, the magnetic inert bodies 18a are collected in a corner of the reaction vessel 26a by means of the magnet unit 24a and thus removed from a detection region in order to facilitate a readout by means of optical techniques. In an alternative embodiment, the magnetic inert bodies 18a can be completely removed from the reaction vessel 26a by means of the magnet unit 24a. In a further alternative embodiment, positioning of the mixing bodies implemented as magnetic inert bodies 18a for a readout can be brought about by means of artificially generated gravity, for example by centrifugation. With respect to a readout, the intensity of the color change within the detection region in the reaction vessel 26a is determined by means of optical techniques and compared with reference measurements in order to determine the analyte quantitatively.

FIGS. 2 to 5 show four further exemplary embodiments of the invention. The descriptions which follow and the drawings are essentially limited to the differences between the exemplary embodiments, and with regard to similarly designated components, especially with respect to components having the same reference signs, reference is made in principle also to the drawings and/or the description of the other exemplary embodiments, especially FIG. 1. For the purposes of distinguishing the exemplary embodiments, the letter a is placed after the reference signs of the exemplary embodiment in FIG. 1. In the exemplary embodiments of FIGS. 2 to 5, the letter a is replaced by the letters b to e.

FIG. 2 shows a method for performing a biochemical analysis, in which two different analytes in a sample 12b are determined. Use is made of a first and a second analyte-specific pair of binding substances 14b, 16b and detection substances 20b, 22b, which are intended for determination of in each case at least two different analytes of the sample 12b. The detection substances 20b, 22b each bear bound to themselves an identical labeling substance, but in principle the detection substances 20b, 22b can also bear bound to themselves different labeling substances. In a first method step, the analyte-specific binding substances 14b, 16b are contained in the reaction vessel 26b in an at least substantially anhydrous form, in which the binding substances 14b, 16b contain sufficient residual water for maintenance of a biological function, bound to magnetic carrier bodies 30b, 32b. In a further method step, the sample 12b, the detection substances 20b, 22b with the labeling substance and further auxiliaries are added in the form of a solution, bringing the binding substances 14b, 16b on the carrier bodies 30b, 32b into solution and making them available for mixing and reaction with the analytes.

In a further method step, the mixing is brought about by means of mixing bodies, which are implemented as the magnetic carrier bodies 30b, 32b for the analyte-specific binding substances 14b, 16b. To this end, the magnetic carrier bodies 30b, 32b are set in motion by means of a magnet unit 24b in the manner already described with respect to FIG. 1. After the mixing and a defined, analyte-dependent period, the analyte-specific binding substances 14b, 16b and detection substances 20b, 22b with the labeling substance have formed analyte complexes 34b, 36b with the analytes of the sample 12b. Signal generation by the labeling substance is achieved as in the preceding example. For facilitation of an optical readout, the magnetic carrier bodies 30b, 32b with the analyte complexes 34b, 36b are positioned in a detection region on an edge of the reaction vessel 26b by means of the magnet unit 24b. In a further alternative embodiment, positioning of the magnetic carrier bodies 30b, 32b with the analyte complexes 34b, 36b for a readout can be brought about by means of artificially generated gravity, for example by centrifugation. The magnetic carrier bodies 30b, 32b for the analyte-specific binding substances 14b, 16b are distinguishable from one another in a readout, such that the two analytes can be determined qualitatively and quantitatively by readout of the detection region by means of optical techniques known in principle. In an alternative embodiment, the magnetic carrier bodies 30b, 32b can bear bound to themselves the detection substances 20b, 22b.

In a further exemplary embodiment (FIG. 3), in a first method step, two analyte-specific detection substances 20c, 22c in a substantially anhydrous form are bound to surfaces of a reaction vessel 26c. In a further method step, a sample 12c and also binding substances 14c, 16c bound to magnetic carrier bodies 30c, 32c, the labeling substance and further auxiliaries such as a solvent for the detection substances 20c, 22c are added in a solution to the reaction vessel 26c. By means of the solvent, the detection substances 20c, 22c are brought into solution, and as a result they detach from the surface of the reaction vessel 26c and the analyte-specific detection substances 20c, 22c can in each case bind to different analytes and on their part bind the labeling substance. Mixing is brought about by means of the magnetic carrier bodies 30c, 32c, which are set in motion via a magnet unit 24c. The binding substances 14c, 16c, the detection substances 20c, 22c with the labeling substance and also the analytes from the sample 12c form two types of analyte complexes 34c, 36c, which are detected by means of optical techniques. For facilitation of the readout, the carrier bodies 30c, 32c with the analyte complexes 34c, 36c are collected in a detection region on an edge of the reaction vessel 26c. In a further alternative embodiment, positioning of the magnetic carrier bodies 30c, 32c with the analyte complexes 34c, 36c for a readout can be brought about by means of artificially generated gravity, for example by centrifugation.

In a further exemplary embodiment (FIG. 4), on a spatially predefined site of a reaction vessel 26d, undetachably fixed binding substances 14d, 16d are used which, in particular, cannot be detached by added substances. For performance of the biochemical analysis, a sample 12d, the detection substances 20d, 22d with labeling substance bound thereto and further auxiliaries in the form of solutions and also magnetic inert bodies 18d are added to the reaction vessel 26d. Mixing of the sample 12d, the detection substances 20d, 22d with the labeling substance in the reaction vessel 26d is brought about by means of the magnetic inert bodies 18d, which are set in motion by a magnet unit 24d. During and after mixing of the sample 12d and the detection substances 20d, 22d with the labeling substance, the analytes in the sample 12d bind to the analyte-specific binding substances 14d, 16d and the analyte-specific detection substances 20d, 22d with the labeling substance bound thereto, and analyte complexes 34d, 36d are formed composed of the analyte-specific binding substances 14d, 16d, the analyte-specific detection substances 20d, 22d with the labeling substance bound thereto and the respective analytes, which are tightly bound to a spatially predefined site of the reaction vessel 26d owing to the undetachably fixed binding substances 14d, 16d. The binding substances 14d, 16d and the analyte complexes 34d, 36d are thereby fixed to spatially separate sites of the reaction vessel 26d, facilitating a readout and discrimination of the analytes from one another. For further facilitation of the readout, the magnetic inert bodies 18d are positioned by means of the magnet unit 24d on a site of the reaction vessel 26d that is separate from the analyte complexes 34d, 36d, such that they do not obstruct the readout. In a further alternative embodiment, positioning of the mixing bodies implemented as magnetic inert bodies 18d for a readout can be brought about by means of artificially generated gravity, for example by centrifugation.

In a further exemplary embodiment (FIG. 5), a device 10e for performing a biochemical analysis comprises not only a reaction vessel 26e, in which undetachably fixed binding substances 14e, 16e are arranged at a spatially predefined site, and a magnet unit 24e, but also a loading vessel 28e in which two analyte-specific detection substances 20e, 22e with labeling substance bound thereto in a substantially anhydrous form are bound to surfaces during the storage period of the device 10e. When using the method for performing a biochemical analysis, a sample 12e with further auxiliaries in the form of a solution and also magnetic inert bodies 18e are filled into the loading vessel 28e in one method step, bringing the detection substances 20e, 22e with labeling substance bound thereto into solution. The solution composed of detection substances 20e, 22e, the sample 12e and magnetic inert bodies 18e is transferred to the reaction vessel 26e in a further method step, and mixing of the detection substances 20e, 22e, the sample 12e and the binding substances 14e, 16e is brought about by means of the magnetic inert bodies 18e via the magnet unit 24e. Formation of analyte complexes 34e, 36e takes place analogously to formation in the exemplary embodiment according to FIG. 4. A readout is carried out in the same manner as in the exemplary embodiment disclosed in FIG. 4. In a further alternative embodiment, positioning of the mixing bodies implemented as magnetic inert bodies 18e for a readout can be brought about by means of artificially generated gravity, for example by centrifugation.

In FIGS. 2 to 5, use has been made of, in each case, two different analyte-specific binding substances 14b-e, 16b-e and detection substances 20b-e, 22b-e, which are intended for determination of, in each case, at least two different analytes of the samples 12b-e. The aforementioned method can be utilized for analysis of a major number of analytes in a sample by using further analyte-specific binding and detection substances. In FIGS. 1 to 5, the method for performing a biochemical analysis has been carried out under of reduced gravity conditions, on board a spacecraft in outer space; in principle, the methods can also be carried out in Earth orbit, on an asteroid, moon or non-earth planet or else under normal gravity on Earth.

REFERENCE NUMERALS

10a Device
10b Device
10c Device
10d Device
10e Device
12a Sample
12b Sample
12c Sample
12d Sample
12e Sample
14a Binding substance
14b Binding substance
14c Binding substance
14d Binding substance
14e Binding substance
16b Binding substance
16c Binding substance
16d Binding substance
16e Binding substance
18a Inert body
18d Inert body
18e Inert body
20a Detection substance
20b Detection substance
20c Detection substance
20d Detection substance
20e Detection substance
22b Detection substance
22c Detection substance
22d Detection substance
22e Detection substance
24a Magnet unit
24b Magnet unit
24c Magnet unit
24d Magnet unit
24e Magnet unit
26a Reaction vessel
26b Reaction vessel
26c Reaction vessel
26d Reaction vessel
26e Reaction vessel
28e Loading vessel
30b Carrier body
30c Carrier body
32b Carrier body
32c Carrier body
34a Analyte complex
34b Analyte complex
34c Analyte complex
34d Analyte complex
34e Analyte complex
36b Analyte complex
36c Analyte complex
36d Analyte complex
36e Analyte complex

The invention claimed is:

1. A method for determining at least one analyte in a sample in outer space under conditions of reduced gravity, comprising:
 a) providing, in outer space, a device that comprises a reaction vessel and a magnet unit, wherein the reaction vessel comprises a detection region and an undetachably fixed capture antibody that binds to the at least one analyte, the undetachably fixed capture antibody located at a spatially predefined position of the reaction vessel within the detection region;
 b) mixing together the sample, a detection antibody that binds the at least one analyte, and magnetic inert bodies in the reaction vessel to form a complex composed of analyte, fixed capture antibody, and detection antibody;

wherein the detection antibody carries bound to itself an enzyme capable of catalyzing a reaction that generates a detectable signal, wherein the magnetic inert bodies consist of magnetic or magnetizable particles that do not substantially bind to the at least one analyte in the sample, to the fixed capture antibody, or to the detection antibody, wherein the mixing is performed by motion of the magnetic inert bodies caused by application of an alternating magnetic field by the magnet unit, c) using the magnet unit to position the magnetic inert bodies outside the detection region; and d) determining the presence of the complex in the reaction vessel by performing optical techniques to measure the detectable signal to determine the at least one analyte in the sample.

2. The method of claim 1, wherein in step c), the magnetic inert bodies are positioned in a corner of the reaction vessel outside of the detection region.

* * * * *